United States Patent
Bednarek et al.

(10) Patent No.: US 8,114,110 B2
(45) Date of Patent: Feb. 14, 2012

(54) TRANSSEPTAL PUNCTURE NEEDLE AND NEEDLE ASSEMBLIES

(75) Inventors: Michael C. Bednarek, Buffalo, MN (US); Ravisankar Gurusamy, Eagan, MN (US); Hans Schnellmann, Lausanne (CH); Todd Stangenes, Minneapolis, MN (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 404 days.

(21) Appl. No.: 12/117,675

(22) Filed: May 8, 2008

(65) Prior Publication Data
US 2009/0171276 A1    Jul. 2, 2009

Related U.S. Application Data

(63) Continuation-in-part of application No. 11/646,525, filed on Dec. 28, 2006, and a continuation-in-part of application No. 10/947,817, filed on Sep. 22, 2004, now Pat. No. 7,635,353.

(60) Provisional application No. 60/916,565, filed on May 8, 2007, provisional application No. 60/800,854, filed on May 17, 2006.

(51) Int. Cl.
*A61B 17/34* (2006.01)
(52) U.S. Cl. ............... 606/185; 606/170; 604/272
(58) Field of Classification Search ........... 606/185, 606/191, 170; 604/170.03, 272, 264, 164.1, 604/164.06, 170.01, 164.08, 96.01, 164.13, 604/164.11, 273, 274; 600/466
See application file for complete search history.

(56) References Cited

U.S. PATENT DOCUMENTS

| 4,561,445 | A | * | 12/1985 | Berke et al. ............... 600/372 |
| 5,224,470 | A | | 7/1993 | Schnepp-Pesch et al. |
| 5,273,532 | A | | 12/1993 | Niezink et al. |
| 5,281,218 | A | | 1/1994 | Imran |
| 5,292,310 | A | * | 3/1994 | Yoon ..................... 604/158 |

(Continued)

FOREIGN PATENT DOCUMENTS
WO    9510319    4/1995
(Continued)

OTHER PUBLICATIONS

International European Search Report Application No. 07009812.4-1526 dated Feb. 29, 2008.

(Continued)

*Primary Examiner* — Ryan Severson
*Assistant Examiner* — Tin Nguyen
(74) *Attorney, Agent, or Firm* — Wiley Rein LLP

(57) ABSTRACT

A transseptal needle includes an elongate needle body having a distal end and a proximal end and a cannular needle tip located proximate the distal end of the needle body. The needle tip has a distal segment, a proximal segment, and a longitudinal axis. An inner surface of the needle tip defines a passageway spanning at least a portion of the needle tip, and an outer surface of the needle tip defines a wall with the inner surface. The distal segment of the needle tip also includes a wedge surface and a dome-shaped region. The wedge surface forms a wedge angle of other than 90 degrees relative to the longitudinal axis. The dome-shaped region, which intersects the wedge surface, includes at least two bevels that intersect the wedge surface and that intersect each other at one or more points on the needle tip.

23 Claims, 12 Drawing Sheets

U.S. PATENT DOCUMENTS

| | | | |
|---|---|---|---|
| 5,330,443 A * | 7/1994 | Powles et al. | 604/240 |
| 5,403,311 A | 4/1995 | Abele et al. | |
| 5,405,376 A | 4/1995 | Mulier et al. | |
| 5,431,649 A | 7/1995 | Mulier et al. | |
| 5,507,802 A | 4/1996 | Imran | |
| 5,628,734 A | 5/1997 | Hatfalvi | |
| 5,807,395 A | 9/1998 | Mulier et al. | |
| 5,906,613 A | 5/1999 | Mulier et al. | |
| 5,910,129 A | 6/1999 | Koblish | |
| 5,928,208 A | 7/1999 | Chu et al. | |
| 5,945,070 A | 8/1999 | Kath et al. | |
| 5,992,899 A | 11/1999 | Strowe | |
| 6,048,329 A | 4/2000 | Thompson et al. | |
| 6,053,904 A | 4/2000 | Scribner et al. | |
| 6,071,274 A | 6/2000 | Thompson et al. | |
| 6,071,279 A | 6/2000 | Whayne et al. | |
| 6,076,012 A | 6/2000 | Swanson et al. | |
| 6,187,019 B1 | 2/2001 | Stefanchik et al. | |
| 6,200,315 B1 | 3/2001 | Gaiser et al. | |
| 6,203,525 B1 | 3/2001 | Whayne et al. | |
| 6,330,473 B1 | 12/2001 | Swanson et al. | |
| 6,402,746 B1 | 6/2002 | Whayne et al. | |
| 6,454,758 B1 | 9/2002 | Thompson et al. | |
| 6,595,958 B1 * | 7/2003 | Mickley | 604/164.01 |
| 6,958,056 B2 | 10/2005 | Kadziauskas et al. | |
| 7,025,766 B2 | 4/2006 | Whayne et al. | |
| 2002/0099335 A1 | 7/2002 | Zohmann | |
| 2003/0028147 A1 * | 2/2003 | Aves et al. | 604/164.06 |
| 2004/0039338 A1 | 2/2004 | Lee | |
| 2004/0092879 A1 | 5/2004 | Kraus et al. | |
| 2005/0020988 A1 | 1/2005 | Woehr et al. | |
| 2005/0085883 A1 | 4/2005 | Ollivier et al. | |
| 2005/0149097 A1 | 7/2005 | Regnell et al. | |
| 2005/0222554 A1 | 10/2005 | Wallace et al. | |
| 2006/0095022 A1 | 5/2006 | Moll et al. | |
| 2006/0100610 A1 | 5/2006 | Wallace et al. | |

FOREIGN PATENT DOCUMENTS

WO      2006039531 A      4/2006

OTHER PUBLICATIONS

International Standard: Steril Hypodermic Needles for Single Use, ISO Reference No. 7864: 1993(E).

* cited by examiner

| Sample Identifier | Outer Needle Tube Dimensions OD/ID x L, mm (inches) | Inner Needle Tube Dimensions OD/ID x L, mm (inches) | Entrance Diameter at Proximal End of Inner Needle Tube, mm (inches) | Entrance Diameter at Proximal End of Outer Needle Tube, mm (inches) | Length of Conjoined Outer and Inner Needle Tubes, mm (inches) | Height of Overall Needle Curvature, mm (inches) | Radius of Overall Needle Curvature, mm (inches) | Length of Exposed Portion of Conjoined Inner and Outer Needle Tubes, mm (inches) | Works with These Sample Stylets (see Fig. 42) |
|---|---|---|---|---|---|---|---|---|---|
| a | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 715 ±2 (28.150 ±.078) | 20 ±0.2 (.787 ±.008) | 48 ±2 (1.89 ±.078) | 710 ±2 (27.953 ±.078) | B |
| b | 1.2/0.8 x 769 (.047/.0315 x 30.28) | 0.8/0.5 x 99 (.0315/.0197 x 3.90) | 0.7 ±0.05 (.028 ±.002) | 1.1 ±0.05 (.043 ±.002) | 783 ±2 (30.835 ±.078) | 55 ±0.2 (2.170 ±.008) | 54 ±2 (2.125 ±.078) | 778 ±2 (30.635 ±.078) | C |
| c | 1.1/0.7 x 551 (.043/.0276 x 21.69) | 0.7/0.4 x 99 (.0276/.0157 x 3.90) | 0.6 ±0.05 (.024 ±.002) | 1 ±0.05 (.039 ±.002) | 565 ±2 (22.244 ±.078) | 20 ±0.2 (.787 ±.008) | 48 ±2 (1.89 ±.078) | 560 ±2 (22.047 ±.078) | A |
| d | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 715 ±2 (28.150 ±.078) | 55 ±0.2 (2.170 ±.008) | 54 ±2 (2.125 ±.078) | 710 ±2 (27.953 ±.078) | B |
| e | 1.1/0.7 x 551 (.043/.0276 x 21.69) | 0.7/0.4 x 99 (.0276/.0157 x 3.90) | 0.6 ±0.05 (.024 ±.002) | 1 ±0.05 (.039 ±.002) | 565 ±2 (22.244 ±.078) | 19 ±0.2 (.746 ±.008) | 30 ±2 (1.193 ±.078) | 560 ±2 (22.047 ±.078) | A |
| f | 1.2/0.8 x 701 (.047/.0315 x 27.60) | 0.8/0.5 x 99 (.0315/.0197 x 3.90) | 0.7 ±0.05 (.028 ±.002) | 1.1 ±0.05 (.043 ±.002) | 985 ±2 (38.780 ±.078) | 55 ±0.2 (2.170 ±.008) | 54 ±2 (2.125 ±.078) | 980 ±2 (38.583 ±.078) | D |
| g | 1.2/0.8 x 881 (.047/.0315 x 34.69) | 0.8/0.5 x 99 (.0315/.0197 x 3.90) | 0.7 ±0.05 (.028 ±.002) | 1.1 ±0.05 (.043 ±.002) | 895 ±2 (35.236 ±.078) | 20 ±0.2 (.787 ±.008) | 48 ±2 (1.89 ±.078) | 890 ±2 (35.040 ±.078) | E |

Fig. 5

| Sample Identifier | Length of Working Portion of the Wire Plus Substantially Straight Support Section of the Handle Portion, mm (inches) | Handle Tube Dimensions OD/ID x L, mm (inches) | Entire Wire Dimensions OD x L, mm (inches) | Works with These Sample Needles (see Fig. 41) |
|---|---|---|---|---|
| A | 605 ±2 (23.819 ±.078) | 0.6/0.35 x 56 (.024/.014 x 2.205) | 0.3 x 640 (.012 x 25.197) | c, e |
| B | 755 ±2 (29.724 ±.078) | 0.7/0.4 x 56 (.028/.016 x 2.205) | 0.35 x 790 (.014 x 31.102) | a, d |
| C | 823 ±2 (32.402 ±.078) | 0.7/0.4 x 56 (.028/.016 x 2.205) | 0.35 x 858 (.014 x 33.779) | b |
| D | 1025 ±2 (40.354 ±.078) | 0.7/0.4 x 56 (.028/.016 x 2.205) | 0.35 x 1060 (.014 x 41.732) | f |
| E | 935 ±2 (36.811 ±.078) | 0.7/0.4 x 56 (.028/.016 x 2.205) | 0.35 x 970 (.014 x 38.190) | g |

Fig. 6

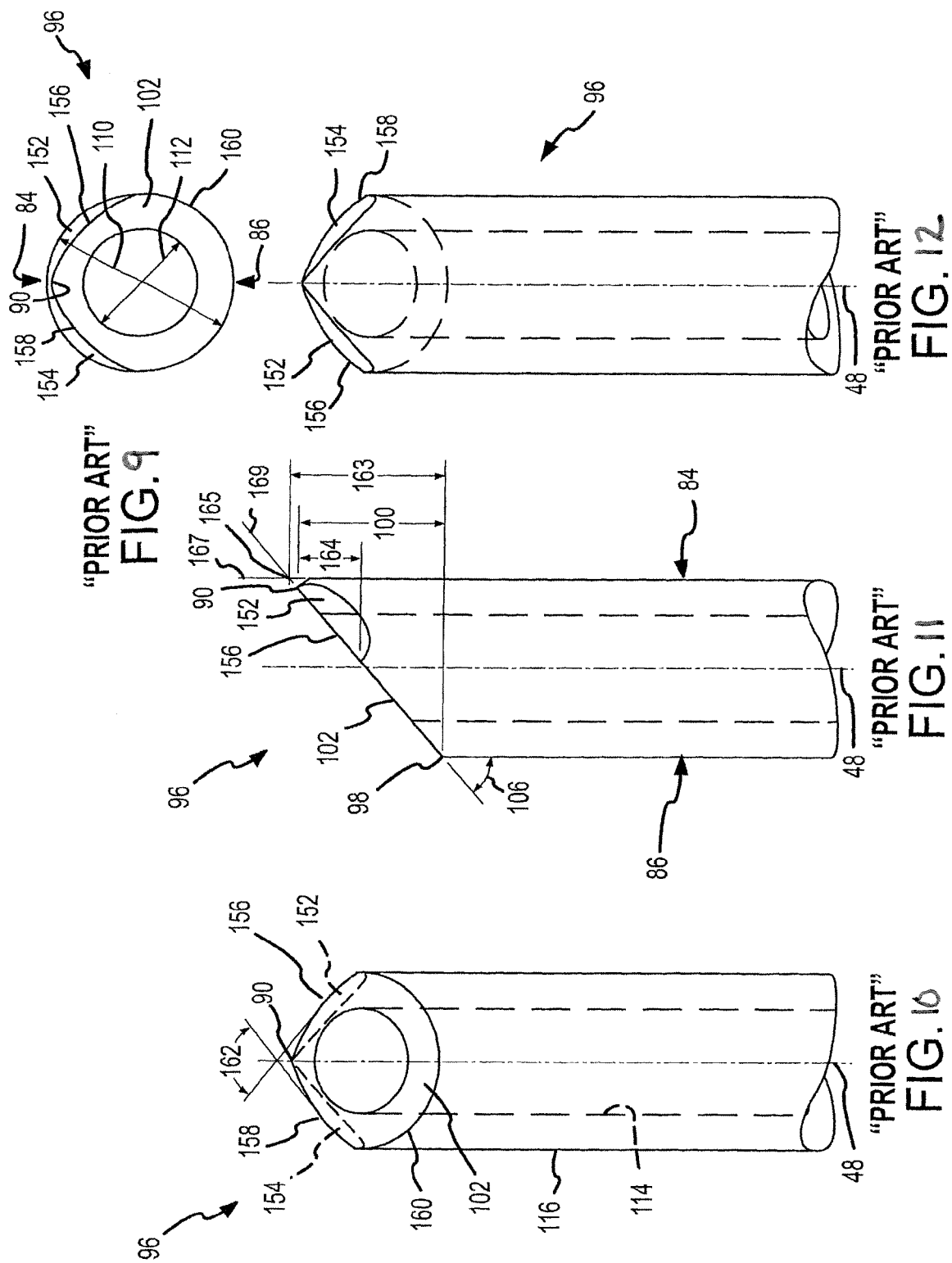

TRANSSEPTAL PUNCTURE NEEDLE AND NEEDLE ASSEMBLIES

CROSS-REFERENCE TO RELATED APPLICATIONS

This application claims the benefit of U.S. provisional application No. 60/916,565, filed May 8, 2007. This application is a continuation-in-part of U.S. application Ser. No. 11/646,525, filed Dec. 28, 2006, which claims the benefit of U.S. provisional application no. 60/800,854, filed May 17, 2006. This application is also a continuation-in-part of U.S. application Ser. No. 10/947,817, filed Sep. 22, 2004. This application is also related to U.S. application Ser. No. 11/647,312, filed Dec. 29, 2006. All of the foregoing are hereby incorporated by reference as though fully set forth herein.

BACKGROUND OF THE INVENTION a. Field of the Invention

The instant invention relates to assemblies and methods for puncturing, or piercing, tissue within the body, including, for example, transseptal access systems and methods for accessing the left atrium from the right atrium by crossing the fossa ovalis. In particular, the instant invention is directed towards transseptal puncture needles and transseptal puncture needle assemblies.

b. Background Art

The human heart includes a right ventricle, a right atrium, left ventricle and left atrium. The right atrium is in fluid communication with the superior vena cava and the inferior vena cava. The tricuspid valve separates the right atrium from the right ventricle. The mitral valve separates the left atrium from the left ventricle. The right atrium is separated from the left atrium by the interatrial septum.

A wide variety of diagnostic and therapeutic procedures have been developed in which a catheter is transluminally advanced within a guide sheath or over a guidewire into various chambers and across valves of the heart. The most difficult chamber of the heart to access with a catheter is the left atrium. Access to the left atrium through the pulmonary artery is not possible. Approaches from the left ventricle are difficult, may cause arrythmias, and may present difficulty in obtaining stable catheter positioning. Accordingly, the most common approach used by electrophysiologists to gain access to the left atrium is through puncture of the interatrial septum from the right atrium.

The objectives of left atrial access can be either diagnostic or therapeutic. One therapeutic use is electrophysiological intervention (e.g., left atrial ablation). Catheter ablation involves the placement of energy (often RF energy) through a catheter, into various locations of the heart to eradicate inappropriate electrical pathways affecting the heart function. When these locations are in the left atrium, the catheter through which the RF generator is placed typically is itself placed through transseptal catheterization.

Transseptal puncture needles are used by physicians who perform specialized invasive cardiology techniques. For example, it is known to access the left atrium using a transseptal approach for catheter ablation of arrythmogenic tissue. During such an approach, a physician may use a transseptal introducer and a long, curved needle for left atrial access from the venous system. The introducer, which may be curved to facilitate access to a desired portion of the left-heart anatomy, includes a sheath and may include a separate dilator. The curved needle may be, for example, a stainless steel Brockenbrough curved needle or a trocar.

The curved needle is used to make the transseptal puncture after the curved transseptal introducer is used to guide the needle into position. In particular, once the transseptal introducer is in the right atrium, the distal tip of the guiding introducer is positioned against a puncture site, such as the fossa ovalis in the inter-atrial septal wall. The Brockenbrough needle is then advanced distally through the transseptal introducer beyond the distal end of the introducer until it punctures the fossa ovalis. If the introducer includes a dilator, the dilator may be advanced with a needle through the punctured fossa ovalis to prepare an access port through the septum and into the left atrium. Once the sheath has been seated across the septum and in the left atrium, the dilator, if present, and the needle may be withdrawn from the sheath. This sheath then provides lumenal access into the left atrium for direct insertion of, for example, a treatment or diagnostic catheter.

To facilitate insertion of the curved needle through the curved transseptal introducer, a stylet may be inserted into the cannula of the needle. The stylet is a flexible rod that stiffens the curved needle and gives it form during its passage through the curved transseptal introducer.

In order to minimize the risk of inadvertently puncturing the left atrial wall just after crossing the septum, it is important that the transseptal puncture needle is sufficiently sharp to reduce the amount of insertion force required. One of ordinary skill in the art can appreciate that, if excessive force is required to insert the needle through the introducer or to puncture the inter-atrial septum, the transseptal puncture needle may inadvertently puncture the atrial free wall, the aorta, the inferior vena cava, or the coronary sinus, for example.

On the other hand, if the needle is too sharp, it may not provide sufficient feedback to the surgeon to let the surgeon know when the needle pierces the inter-atrial septum. In addition, advancement of a sharp needle tip or a needle tip with a sharp edge through the dilator or sheath may cause particles to be skived from the interior surface of the dilator or sheath. Accordingly, it is desirable that the transseptal puncture needle strike a balance between sufficiently sharp to reduce the amount of insertion force required while not so sharp as to cause skiving and/or to provide too little feedback to the surgeon.

BRIEF SUMMARY OF THE INVENTION

The present invention provides assemblies and methods for puncturing, or piercing, tissue within the body, including transseptal needles and transseptal needle assemblies.

An object of the present invention is to provide a transseptal needle that minimizes the force required to puncture septum.

Another object of the present invention is to provide a transseptal needle that reduces the risk of coring during septal penetration.

Yet another object of the present invention is to provide a transseptal needle that minimizes skiving.

Still another object of the present invention is to provide a transseptal needle that provides desirable feedback to the surgeon or surgical system in use.

In a first aspect, the present invention provides a transseptal needle, including: an elongate needle body having a distal end and a proximal end; and a cannular needle tip located proximate the distal end of the elongate needle body, the needle tip having a distal segment, a proximal segment, and a longitudinal axis extending through at least a portion of the distal segment and the proximal segment. The needle tip generally includes: an inner surface defining a passageway spanning at least a portion of the needle tip; an outer surface, the inner surface and the outer surface defining therebetween a wall; a wedge surface at the distal segment of the needle tip, the wedge surface forming a wedge angle of other than 90 degrees relative to the longitudinal axis of the needle tip; a dome-shaped region at the distal segment of the needle tip; a first bevel in the dome-shaped region; and a second bevel in the dome-shaped region, wherein the first bevel and the second bevel intersect at one or more points on the needle tip.

Preferably, the first bevel and the second bevel intersect along a line on the needle tip to form an interbevel angle. The interbevel angle is preferably between about 80 degrees and about 120 degrees, more preferably between about 100 degrees and about 110 degrees, and most preferably about 105 degrees. It is also desirable for the first bevel and the second bevel to intersect at one or more points within the wall, though the first bevel and the second bevel may intersect at one or more points on the inner surface without departing from the scope of the invention.

The dome-shaped region has a depth, which is preferably between about 0.075 mm and about 0.125 mm, and a radius of curvature, which is preferably between about 0.79 mm and about 0.99 mm. More preferably, the dome-shaped region has a depth of about 0.100 mm and a radius of curvature of about 0.89 mm.

The wedge angle is preferably between about 20 degrees and about 50 degrees relative to the longitudinal axis of the needle tip, and more preferably about 30 degrees relative to the longitudinal axis of the needle tip.

In another embodiment, the present invention provides a transseptal needle assembly, including: a tubular elongate needle body terminating in a needle tip. The needle tip may include: an inner surface defining a passageway extending through at least a portion of the needle body including the needle tip; an outer surface; a wedge surface; a dome-shaped surface intersecting the wedge surface; and at least two reverse-angled bevels in the dome-shaped surface, each of the at least two reverse-angled bevels intersecting the wedge surface, wherein the intersection of the at least two reverse-angled bevels and the wedge surface at least partially defines a puncture tip leading edge to facilitate transseptal puncturing. The inner surface and the outer surface define therebetween a wall. Preferably, the puncture tip leading edge is located on an upper surface of the wall.

It is desirable for the at least two reverse-angled bevels to intersect at one or more points within the tubular elongate needle body, such as along a line within the tubular elongate needle body.

Optionally, the transseptal needle assembly further includes a needle hub coupled to the proximal end of the transseptal needle and/or a stylet adapted for insertion through the tubular elongate needle body.

Also disclosed herein is a system for use in transseptal catheterization procedures, the system including: a dilator; a handle assembly including a sheath hub, a dilator hub removably connected to the sheath hub, and a needle hub removably connected to the dilator hub; and a needle assembly, the needle assembly including a transseptal needle having a needle tip. The needle tip typically includes: a wedge surface; a dome-shaped surface intersecting the wedge surface; a first reverse-angle bevel in the dome-shaped surface intersecting the wedge surface; and a second reverse-angle bevel in the dome-shaped surface intersecting the wedge surface and the first reverse-angle bevel. In addition, the system typically includes a needle advancement mechanism adapted to cooperate with the needle assembly, wherein the needle advancement mechanism allows for selective advancement of the needle assembly from a position within the dilator to a position external to the dilator.

In still another embodiment, the present invention includes an elongated, curved transseptal puncture needle, including: a needle proximal end; a needle distal end, wherein the needle distal end comprises a working portion including an inner needle tube and an outer needle tube, wherein the inner needle tube and the outer needle tube are conjoined, wherein the inner needle tube comprises a proximal end and a distal end, wherein the outer needle tube comprises a proximal end and a distal end, wherein the proximal end of the inner needle tube is inserted into the distal end of the outer needle tube, creating an embedded portion and an exposed portion of the inner needle tube, and creating a circumscribing portion and a nonoverlapping portion of the outer needle tube, and wherein the conjoined inner and outer needle tubes define a conjoined outer surface including an outer surface of the outer needle tube plus an outer surface of the exposed portion of the inner needle tube; and a needle tip at the distal end of the inner needle tube. The needle tip may include: a puncture tip leading edge; a puncture tip trailing edge; a wedge surface extending between the puncture tip leading edge and the puncture tip trailing edge; a dome-shaped surface intersecting the wedge surface; and a pair of intersecting reverse-angle bevels in the dome-shaped surface, each of the pair of intersecting reverse-angle bevels intersecting the wedge surface; wherein the puncture tip leading edge is defined by an intersection of the pair of intersecting reverse-angle bevels and the wedge surface.

Also disclosed is a method of manufacturing a transseptal needle, including the following steps: providing a substantially tubular body having a proximal end and a distal end; providing a dome-shaped region proximate the distal end; truncating the substantially tubular body at a wedge angle to create a wedge surface, the wedge surface intersecting the dome-shaped region; and beveling at least one reverse-angle bevel into the dome-shaped region intersecting the wedge surface.

The beveling step may include: beveling a first reverse-angle bevel into the dome-shaped region intersecting the wedge surface; and beveling a second reverse-angle bevel into the dome-shaped region intersecting the wedge surface, wherein the first reverse-angle bevel and the second reverse-angle bevel intersect at an interbevel angle. Preferably, the at least one reverse-angle bevel intersects the wedge surface between an inner diameter of the substantially tubular body and an outer diameter of the substantially tubular body.

The step of providing a dome-shaped region proximate the distal end may include bending the distal end of the substantially tubular body into a curved configuration prior to the truncating step.

An advantage of the present invention is that it reduces the insertion force necessary, thereby minimizing the risk of inadvertently puncturing the left atrial wall just after crossing the septum.

Another advantage of the present invention is that it provides a reduced risk of tissue coring.

Still another advantage of the present invention is that it reduces skiving of dilator and/or sheath particles as the needle is introduced.

A further advantage of the present invention is that it provides desirable tactile feedback to the surgeon or surgical system in use.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 depicts a table of dimensions for seven sample transseptal puncture needles according to the present invention.

FIG. 6 depicts a table of dimension for five sample stylets according to the present invention.

FIG. 9 is an end or top view of the prior art needle tip of FIGS. 7 and 8.

FIG. 10 is a front view of the prior art needle tip of FIGS. 7-9.

FIG. 11 is a side view of the prior art needle tip of FIGS. 7-10, the opposite side view being a mirror image thereof.

FIG. 12 is a rear view of the prior art needle tip of FIGS. 7-11.

DETAILED DESCRIPTION OF THE INVENTION

Figure 1:
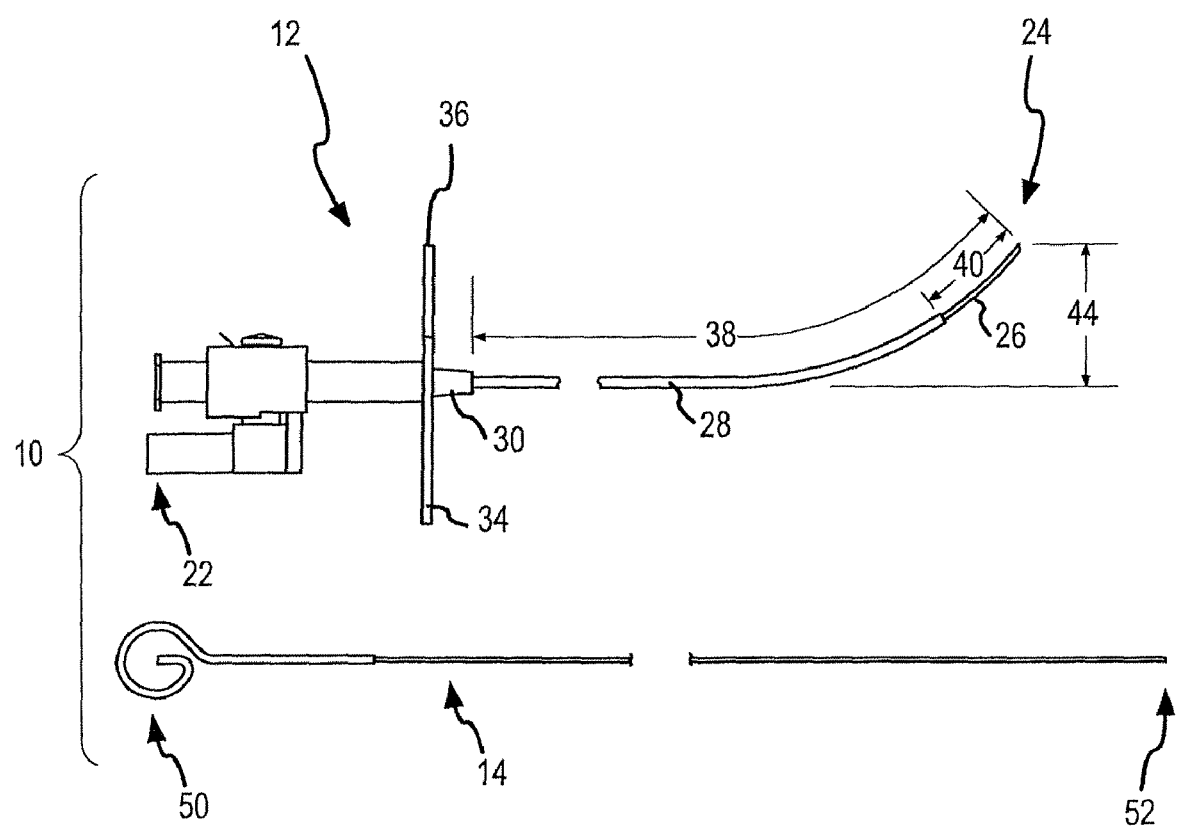
FIG. 1 is a fragmentary, side view of a transseptal puncture needle assembly according to a first embodiment of the present invention, including a transseptal puncture needle and a stylet.

The present invention comprises curved transseptal puncture needles 12 and needle assemblies 10 (i.e., the combination of a curved transseptal puncture needle 12 and its stylet 14 as shown in FIG. 1) that facilitate insertion through curved transseptal introducers 16 (i.e., sheaths, or sheath 18 and dilator 20 combinations as shown in, for example, FIG. 11). The needle assemblies 10 and introducers 16 permit, for example, left atrial access from the venous system for catheter diagnosis and treatment (e.g., ablation of arrhythmogenic cardiac tissue). Each curved transseptal puncture needle 12 has a specific tip configuration and axial orientation, the combination of which is designed to facilitate low force, smooth insertion through the introducer 16 while reducing the risk of introducing dilator particulate removed by the needle tip (e.g., skiving) into a patient's left heart or blood stream, and while reducing the amount of coring that may occur during puncture of the patient's inter-atrial septum.

FIG. 1 depicts a transseptal puncture needle assembly 10 according to the present invention. The transseptal puncture needle assembly 10 comprises a transseptal puncture needle 12 and a stylet 14. The transseptal puncture needle 12 is elongated, having a proximal end 22 and a distal end 24. The working portion of the needle comprises an inner needle tube 26 and an outer needle tube 28, which are conjoined as explained further below. The conjoined inner and outer needle tubes 88 (FIG. 4) are united with a mounting collar 30 that may be seen to good advantage in FIG. 1. For example, the proximal end 32 (FIG. 4) of the conjoined inner and outer needle tubes 88 may be press fit into the mounting collar 30 (e.g., approximately 5 mm) and may be affixed in position by an adhesive. In one embodiment, epoxy is used to join the proximal end 32 of the conjoined inner and outer needle tubes 88 to the mounting collar 30 by applying epoxy to a depth of approximately 0.2 mm. Between the distal end 24 of the transseptal puncture needle 12 and the mounting collar 30 is a shield 34 having a shield point 36. The shield point 36, which is more clearly shown in FIG. 3, indicates the direction of curvature of the transseptal puncture needle 12 (i.e., the conjoined inner and outer needle tubes 88.)

Length 38 is the length of the exposed portion of the conjoined inner and outer needle tubes 88. Similarly, length 40 is the length of the straight, exposed portion 42 (FIG. 4) of the inner needle tube 26. The length 40 of this straight, exposed portion 42 of the inner needle tube 26 is approximately 15±0.2 mm (i.e., 0.590±0.008 inches) in one embodiment of the present invention. Height 44 is the overall height of needle curvature. Sample values for each of these dimensions are presented in the table 46 of FIG. 5. The table 46 of FIG. 5, which is explained further below, includes additional dimensions also. For example, the radius of overall needle curvature is presented in the eighth column from the left in FIG. 5. These sample values for the radii of overall needle curvature refer to the approximate curvature along a needle centerline or longitudinal axis 48 (see FIG. 4) of the curved portion (visible in, for example, FIGS. 1 and 3) of the transseptal puncture needle. This represents the curvature of the right-most portion of the transseptal puncture needle 12 depicted in FIG. 1. As shown to good advantage in FIG. 1, the stylet 14 also includes a proximal end 50 and a distal end 52.

Figure 2:
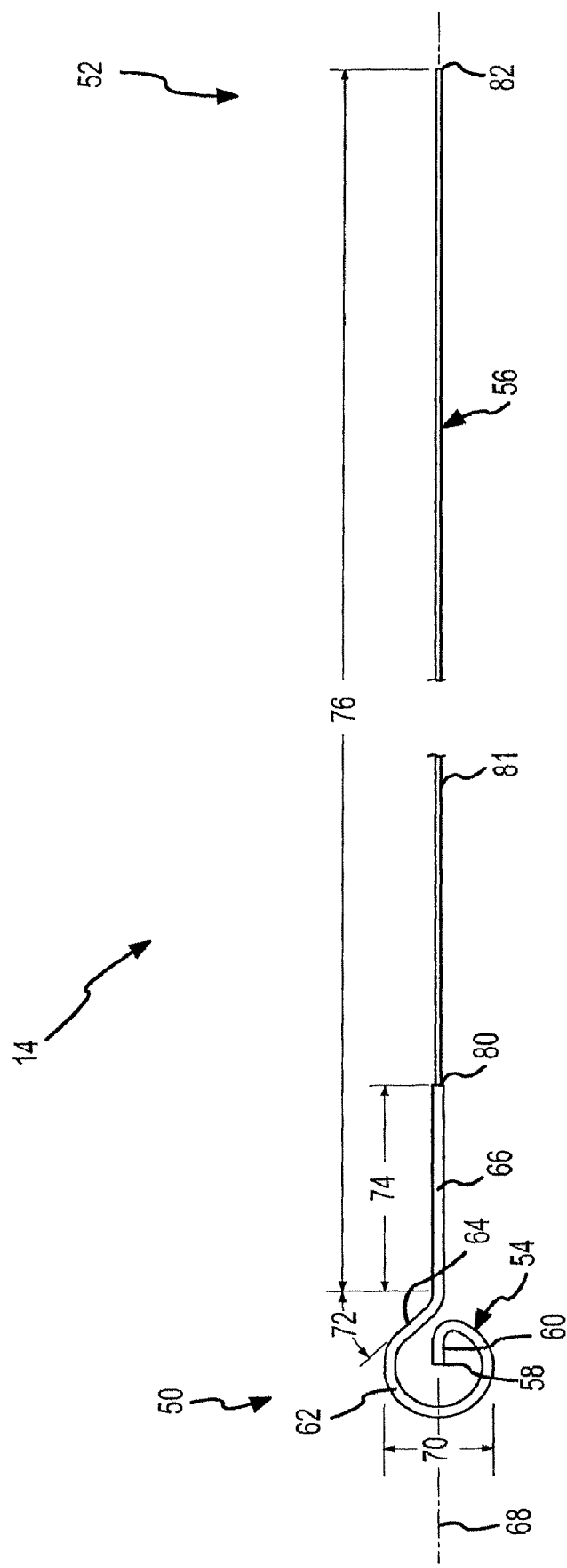
FIG. 2 is an enlarged, fragmentary view of the stylet depicted in FIG. 1.

Referring next to FIG. 2, additional details concerning the stylet 14 are discussed. The proximal end 50 of the stylet includes a handle portion 54, and the distal end 52 of the stylet includes a working portion 56. The handle portion 54 is in the shape of a stylized letter "G" starting at a trailing end 58, continuing with a free end section 60, an arcuate section 62, a transition section 64, and a substantially straight support section 66. The trailing end 58 and free end section 60 are aligned with a stylet centerline 68, and the handle portion 54 overall is essentially centered about the stylet centerline 68. The overall hand height 70 is approximately 10±2 mm (i.e., 0.399 inches) in one embodiment of the present invention. In the depicted embodiment, the transition section 64 connects the arcuate section 62 to the substantially straight support section 66 at a transition angle 72 defined as the angle between the vertical line depicted in FIG. 2 and a line parallel to the longitudinal centerline (not shown) of the transition section. In one embodiment of the present invention, the transition angle 72 is approximately 45°. The transition section joins the substantially straight support section when the transition section 64 curves into the substantially straight support section 66. In one embodiment of the present invention, the transition section 64 curves into the substantially straight support section 66 along a radius of curvature of approximately 2.5 mm (i.e., 0.100 inches). In one embodiment of the present invention, the length 74 of the substantially straight support section 66 is approximately 21 mm (i.e., 0.827 inches). The combined length 76 of the working portion 56 and the substantially straight support section 66 varies depending upon the specific application for the transseptal puncture needle 12. Possible combined length dimensions (i.e., the length of the working portion 56 of the wire, which is the exposed portion of the wire, plus the length of the substantially straight support section 66 of the handle portion 54) for five sample stylets are presented in the second column of the table 78 in FIG. 6.

The handle portion 54 may be made from, for example, AISI 304 stainless steel tubing. Sample dimensions for sections of tubing that may be shaped into the handle portion 54 are presented in the third column of the table 78 of FIG. 6. In the third column, the dimensions are presented as OD/ID×L, wherein "OD" is the outer diameter of the tubing, "ID" is the inner diameter of the tubing, and "L" is the length of the tubing. All dimensions are provided once in millimeters with the same information presented parenthetically in inches. The sample outer diameter dimensions presented in the third column in FIG. 6 have the following tolerances in one embodiment: ±0.01 mm (i.e., ±0.0004 inches). Similarly, the tolerances for the sample inner diameter dimensions presented in the third column of FIG. 6 are as follows: +0.03 mm and −0 mm (i.e., +0.001 inches and −0 inches). The substantially straight support section 66 of the handle portion 54 terminates distally at a leading end 80. Preferably, there is no play between the handle portion 54 and the working portion 56 at the leading end 80 and break edges are present (i.e., the leading end 80 is preferably blunt with rounded edges).

Continuing to refer to FIG. 2, the working portion 56, which is the exposed part of a stylet wire 81 that extends into the handle portion 54, terminates distally at a leading end 82 that is blunt with rounded edges. In one embodiment of the present invention, the wire 81 comprising the working portion 56 is AISI 302 stainless steel wire. Some possible overall lengths for this wire are presented in the fourth column of the table 78 of FIG. 6. The dimensions in each sample entry in the fourth column are presented as OD×L, where "OD" is the outer diameter of the wire, and "L" is the total length of the entire wire, including the working portion 56 and the portion embedded in the handle portion 54. These dimensions are again provided in millimeters with their equivalents in inches presented in parentheticals. The length dimensions provided in the fourth column of FIG. 6 have the following tolerances: +0 mm and −0.015 mm (i.e., +0 inches and −0.0006 inches). The fifth column of the table presented in FIG. 6 provides compatibility information for the sample needles from FIG. 5 with which the stylets of FIG. 6 may be used. For example, the stylet with sample identifier "A" in FIG. 6 may be used with sample needles "c" or "e" of FIG. 5. For the sample stylet embodiments presented in FIG. 6 and depicted in FIG. 2, approximately 56 mm of the wire resides within the tubing comprising the handle portion 54. Thus, a distal portion of the wire comprises the working portion 56 of the stylet 14, and a proximal portion of the wire extends into the handle portion 54 of the stylet 14 along and proximally past the proximal end of the substantially straight support section 66 of the handle portion 54. Since a portion of the wire comprising the working portion 56 of the stylet 14 extends into at least a part of the handle portion 54 of the stylet 14, the outer diameter of the wire must be selected to fit within the inner diameter of the tubing comprising the handle portion 54. In the sample information presented in FIGS. 5 and 6, the outer diameter of the wire is selected to be approximately 0.05 mm smaller than the inner diameter of the tubing comprising the handle portion 54. Thus, the wire fits into the tubing, but the play is minimized between the wire and the tubing.

The table 78 presented in FIG. 6 provides dimension data for five sample stylets according to the present invention. The first column presents a sample identifier. The second column presents the length of the working portion of the wire (i.e., the exposed portion of the wire) plus the length of the substantially straight support section 66 of the handle portion 54. In other words, the sample lengths presented in the second column of the table of FIG. 6 represent the distance from the leading end 82 of the stylet wire, which coincides with the distal end 52 of the stylet 14, to the proximal end of the substantially straight support section 66 of the handle portion 54 of the stylet 14. The third column represents sample dimensions for the tubing from which the handle portion 54 may be formed. These numbers represent the possible dimensions for a section of tubing that may be shaped to form the handle portion 54. The number to the left of the slash represents the outer diameter of this tubing, the number to the right of the slash represents the inner diameter of this tubing, and the third number represents the length of the tubing. The dimensions are provided in millimeters, with the corresponding dimensions in inches provided parenthetically. The fourth column of FIG. 6 provides dimension information for sample wires, with the first dimension being the outer diameter of the wire and the second dimension being the overall length of the wire. Again, the numbers are provided in millimeters with the inch equivalents following in parentheticals. The sample length dimensions in this fourth column represent the overall length of the wire that comprises the working portion 56 of the stylet 14, including the part of the wire that is embedded in the hollow handle portion 54. It should be noted that samples "B," "D," and "E" are considered dimensions for an adult stylet. Sample "A" presents dimensions for a pediatric stylet, and sample "C" presents dimensions for an atrial mapping and ablation system (AMAS) stylet. The length of exposed wire (i.e., the length of the working portion 56 of the stylet 14 to the right of the leading end 80 of the substantially straight support section 66 of the handle portion 54 as depicted in FIG. 2) for the sample dimensions presented above or as follows: approximately 584 mm for stylet "A," approximately 734 mm for stylet "B," approximately 802 mm for stylet "C," approximately 1004 mm for stylet "D," and approximately 914 mm for stylet "E."

Figure 3:
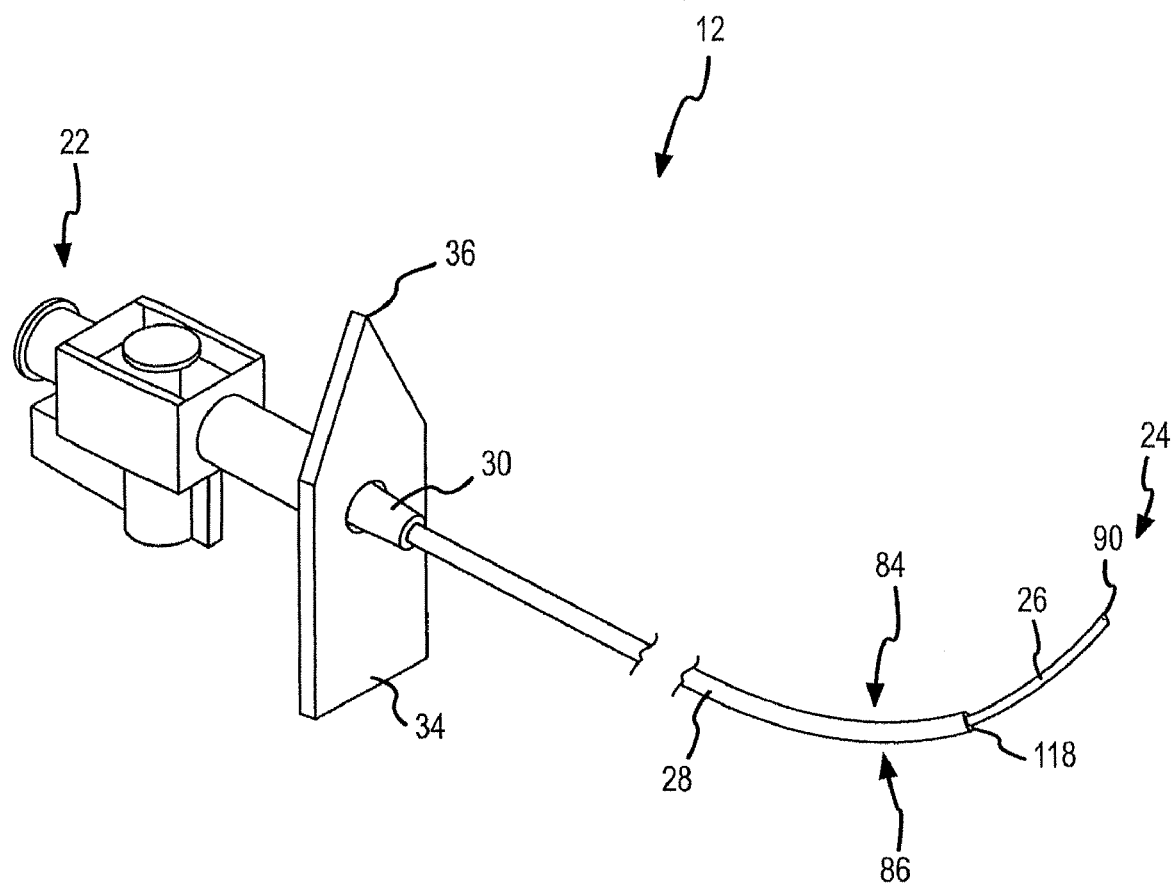
FIG. 3 is a slightly enlarged, fragmentary, isometric view of the curved transseptal puncture needle depicted in FIG. 1.

FIG. 3 is a slightly enlarged, fragmentary isometric view of the curved transseptal puncture needle 12 depicted in FIG. 1. This depiction of the transseptal puncture needle clearly shows how the shield point 36 indicates the direction of curvature of the needle 12. As shown in FIG. 3, the transseptal puncture needle 12 has a first side 84 in a second side 86. The first side 84 comprises the outer surface of the conjoined inner and outer needle tubes 88 (FIG. 4) extending longitudinally along and including that portion of the outer surface of the inner needle tube 26 that extends most closely adjacent to a puncture tip leading edge 90. The first side 84 may also be seen to good advantage in FIG. 4. The second side 86 is that portion of the outer surface of the conjoined inner and outer needle tubes 88 that is radially offset from the first side 84 by 180°. Again, the second side 86 of the transseptal puncture needle 12 is also clearly labeled in FIG. 4.

Figure 4:
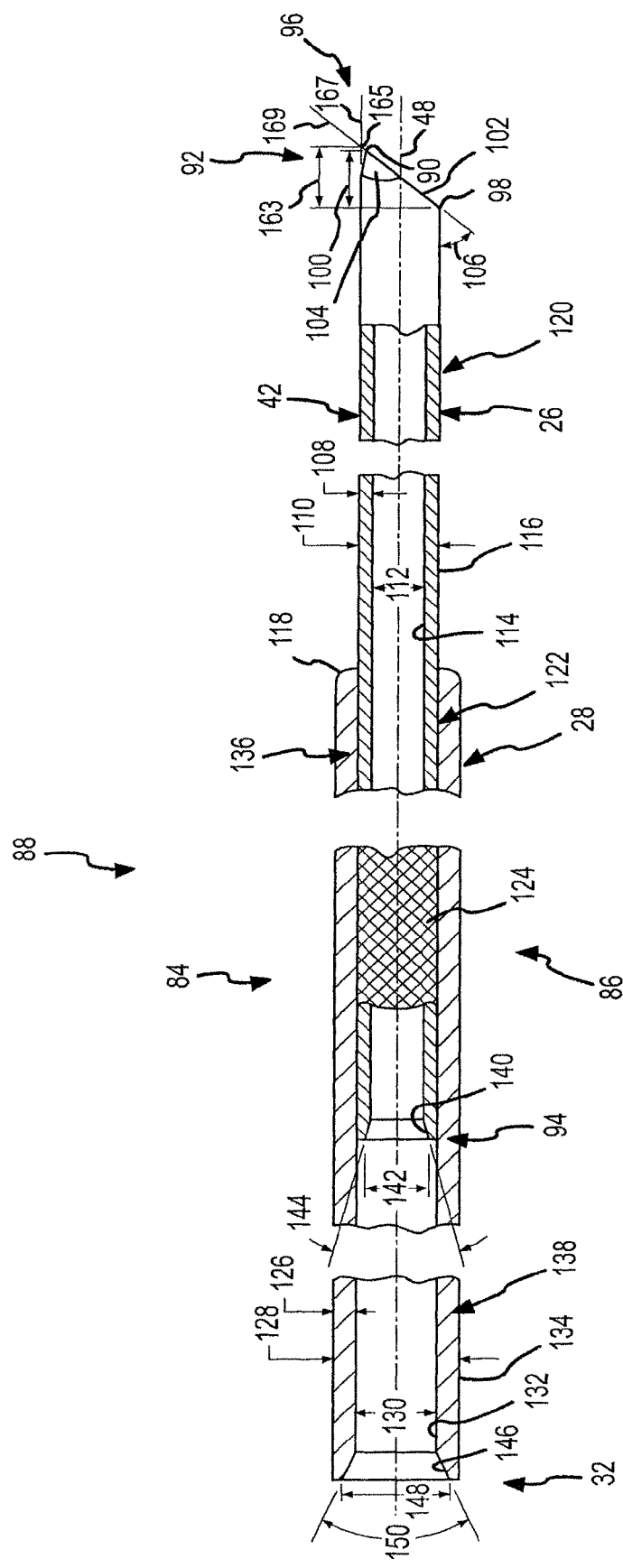
FIG. 4 is a fragmentary view in partial cross section of the basic configuration of the conjoined inner needle tube and outer needle tube of the curved transseptal puncture needle, and shows the needle with the needle tip configuration and orientation according to the first embodiment of the present invention, which is also depicted in FIGS. 1 and 3.

FIG. 4 is an enlarged, isometric view of the conjoined inner and outer needle tubes 88 of the transseptal needle 12 depicted in FIGS. 1 and 3 broken away from the remaining parts of the transseptal needle 12 for clarity. The outer needle tube 28 and the inner needle tube 26 may each comprise AISI 304 stainless steel tubing. The inner needle tube 26 comprises a distal end 92 and a proximal end 94. The distal end 92 of the inner needle tube 26 includes a needle tip 96 having the puncture tip leading edge 90 and a puncture tip trailing edge 98. The distance measured parallel to the needle's centerline 48 from the puncture tip leading edge 90 to the puncture tip trailing edge 98 is the needle tip length 100, and a tip wedge surface 102 is defined between the puncture tip leading edge 90 and the puncture tip trailing edge 98. The wedge surface 102 may be finished, for example, by sandblasting. In the embodiment depicted in FIG. 4, the needle tip 96 has a prior art configuration including a tangential back bevel 104, which may be better seen in FIGS. 7-12. The specifics of this tip configuration are explained further below.

In the needle tip depicted in FIGS. 4 and 7-12, the tip wedge surface 102 forms a wedge surface angle 106 of approximately 50°. The inner needle tube 26 has an inner tube thickness 108, an inner tube outer diameter 110, and an inner tube inner diameter 112. The inner needle tube 26 also comprises an inner surface 114 and an outer surface 116. Since the proximal end 94 of the inner needle tube 26 is inserted into a distal end 118 of the outer needle tube 28, the inner needle tube 26 also comprises an exposed portion 120 and an embedded portion 122. In an embodiment of the present invention, the embedded portion 122 of the inner needle tube 26 is approximately 83 mm long and is secured within the outer needle tube 28 by adhesive 124 as described further below.

The outer needle tube 28 extends from the distal end 118 of the outer needle tube 28 to a proximal end 32 of the outer needle tube 28. Similar to the inner needle tube 26, the outer needle tube 28 has an outer tube thickness 126, an outer tube outer diameter 128, an outer tube inner diameter 130, an inner surface 132, and an outer surface 134. Since the outer needle tube 28 does overlap with the embedded portion 122 of the inner needle tube 26, the outer needle tube 28 further comprises a circumscribing portion 136, which is the portion of the outer needle tube 28 that extends around the embedded portion 122 of the inner needle tube 26, and a nonoverlapping portion 138, which is the remainder of the outer needle tube 28. The distal end 118 of the outer needle tube 28 is blunt with rounded edges.

The proximal end 94 of the inner needle tube 26 is configured similarly to the proximal end 32 of the outer needle tube 28. In particular, a frustal entrance surface 140 extends from the inner surface 114 of the inner needle tube 26 to the proximal end 94 of the inner needle tube 26. Where this frustal entrance surface 140 meets the proximal end 94 of the inner needle tube 26, an entrance diameter 142, which is slightly small than the outer diameter 110 of the inner needle tube 26 is present. The walls of the frustal entrance surface 140 form an entrance angle 144 of approximately 60° in one embodiment. Similarly, a frustal entrance surface 146 extends from the inner surface 132 of the outer needle tube 28 to the proximal end 32 of the outer needle tube 28, thereby defining an entrance diameter 148 that is slightly smaller than the outer diameter 128 of the outer needle tube 28. Again, the surfaces of the frustal entrance surface 146 at the proximal end 32 of the outer needle tube 28 form an entrance angle 150 of approximately 60°.

Thus, FIG. 4 depicts the basic configuration of the conjoined inner and outer needle tubes 88 of the transseptal puncture needle. This basic configuration may be used for the transseptal puncture needles 12 described herein, even though FIG. 4 depicts a specific configuration for the puncture tip leading edge 90. The remainder of this specification thus does not redescribe the baseline configuration of the conjoined inner and outer needle tubes 88, and focuses on the configuration of the needle tip at the distal end 92 of the inner needle tube 26.

To join the embedded portion 122 of the inner needle tube 26 within the circumscribing portion 136 of the outer needle tube 28, the embedded portion 122 may be sandblasted and epoxy may be applied to approximately 68 mm (2.68 inches) of the embedded portion 122. Thus, of the approximately 83 mm of overlap, epoxy may be applied to approximately 68 mm.

As mentioned above, the table 46 of FIG. 5 provides dimension data for seven sample transseptal puncture needles according to the present invention. Each of these needles could have one of the needle tips discussed herein and would be used with an appropriately dimensioned introducer 16 and stylet 14. The first column of the table presented in FIG. 5 is a sample identifier. The second column of the table presents outer needle tube dimensions. These outer needle tube dimensions are represented as OD/ID×L, wherein "OD" is the outer diameter 128 of the outer needle tube 28, "ID" is the inner diameter 130 of the outer needle tube 28, and "L" is the overall length of the outer needle tube. The tolerance for the noted outer needle tube 28 outer diameters 128 is ±0.015 mm (i.e., ±0.0006 inches). Similarly, the inner diameter 130 dimensions presented in FIG. 5 for the outer needle tube 28 have tolerances of +0.04 mm and −0 mm (i.e., +0.0015 inches and −0 inches). The third column of the table presented in FIG. 5 represents sample inner needle tube dimensions. In the third column, the dimensions are again presented as OD/ID× L, wherein "OD" is the outer diameter 110 of the inner needle tube 26, "ID" is the inner diameter 112 of the inner needle tube 26, and "L" is the overall length of the sample inner needle tubes. With regard to the inner needle tube dimensions presented in FIG. 5, the outer diameters 110 presented are ±0.01 mm (i.e., ±0.004 inches) in one embodiment of the present invention. The tolerances for the inner diameters 112 of the inner needle tube 26 are +0.03 mm and −0 mm (i.e., +0.001 inches and −0 inches. In another embodiment or sample, the inner needle tubes are 98±2 mm (i.e., 3.858±0.078 inches).

The fourth column of the table 46 presented in FIG. 5 presents sample data for the entrance diameter 142 at the proximal end 94 of the inner needle tube 26. These sample entrance diameters 142 are presented as length in millimeters±a tolerance value. The equivalent dimensions are presented parenthetically in inches. The fifth column of the same table presents sample entrance diameter 148 information at the proximal end 32 of the outer needle tube 28. Again, this data is presented as length in millimeters±a tolerance value in millimeters, with the corresponding dimensions in inches presented parenthetically. The sixth column of the table presents sample information concerning the overall length of the conjoined outer and inner needle tubes 88, measured from the puncture tip leading edge 90 to the proximal end 32 of the outer needle tube 28. This sample length data is presented as a value in millimeters±a tolerance in millimeters, with the corresponding dimensions presented parenthetically in inches.

The seventh column of table 46 (FIG. 5) presents sample dimensions for the height 44 of the overall needle curvature (see FIG. 1), presented as length in millimeters±a tolerance value in millimeters with the equivalent dimensions in inches presented parenthetically. The eighth column of the table 46 presented in FIG. 5 presents sample dimensions for the radius of overall needle curvature. These values represent the approximate radius of curvature of the needle 12 and are presented as a value in millimeters±a tolerance in millimeters with the corresponding dimensions in inches provided parenthetically. The ninth column of this table presents sample dimensions for the length 38 of the exposed portion of the conjoined inner and outer needle tubes 88 (i.e., the overall length from the distal side of the mounting collar 30 to the puncture tip leading edge 90. These sample lengths 38 are presented in millimeters with a tolerance value also provided in millimeters. Equivalent dimensions in inches are provided parenthetically. The tenth column of the table presented in FIG. 5 ties this information to that provided for stylets in FIG. 6. For example, the needle having sample identifier "a" in FIG. 5 works with the stylet having sample identifier "B" in FIG. 6. It should also be noted that samples "a," "d," "f," and "g" presented in FIG. 5 are considered adult transseptal puncture needles. Samples "c" and "e" are considered pediatric transseptal puncture needles, and sample "b" is an AMAS needle.

Figure 7:
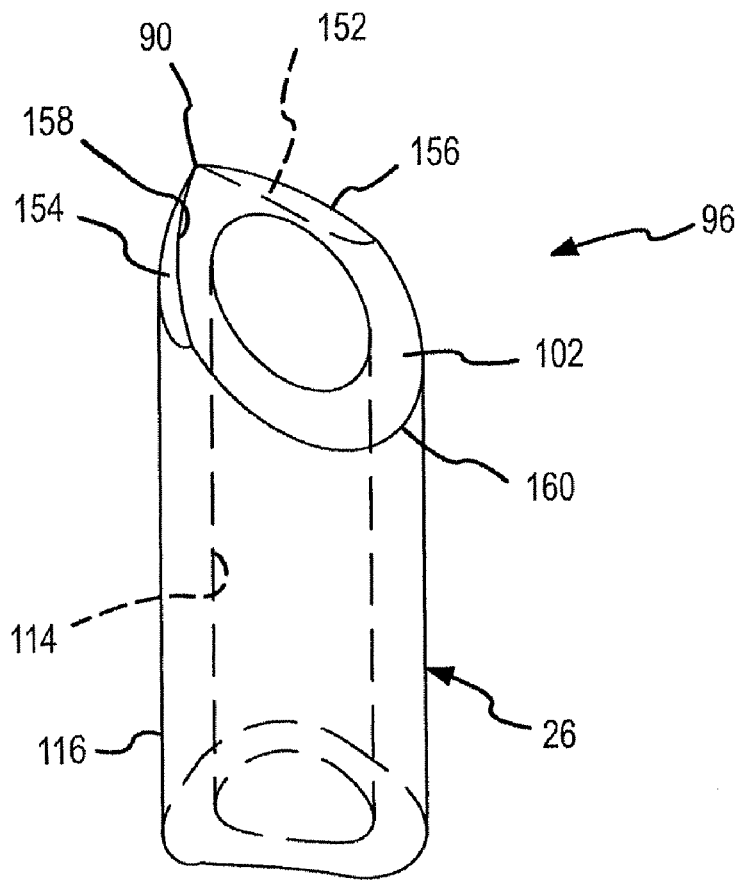
FIG. 7 is an enlarged, isometric view of a transseptal puncture needle having a prior art needle tip with a tangential back bevel configuration.
Figure 8:
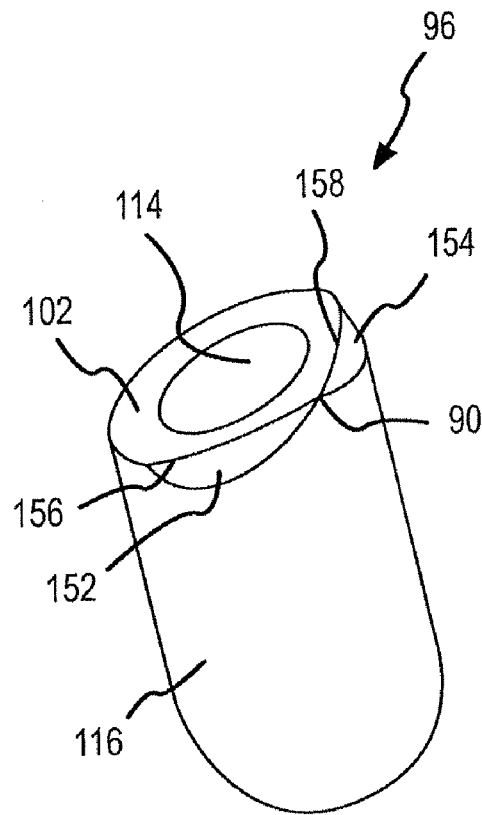
FIG. 8 is a second enlarged, isometric view of the prior art needle tip of FIG. 7.

FIGS. 7-12 depict a needle tip 96 having a prior art configuration. In particular, the needle tip 96 depicted in these figures has a tangential back bevel configuration, comprising a first tangential back bevel 152 and a second tangential back bevel 154. As shown in FIG. 7, which is an enlarged, isometric view of the prior art needle tip 96, the needle tip includes a puncture tip leading edge 90 and a wedge surface 102. A first cutting edge 156 is defined where the first tangential back bevel 152 meets the wedge surface 102, and a second cutting edge 158 is defined where the second tangential back bevel 154 meets the wedge surface 102. The outer surface 116 of the inner needle tube 26 and the inner surface 114 of the inner needle tube 26 are also labeled in FIG. 7. FIG. 8 is a second enlarged, isometric view of the same prior art needle tip 96. This figure shows the same features just described with reference to FIG. 7 from a different angle.

FIG. 9 is an end or top view of the prior art needle tip 96 depicted in FIGS. 4, 7, and 8. As depicted in this figure, the wedge surface 102 is defined by an arcuate edge 160 that joins the first cutting edge 156 and the second cutting edge 158. The inner diameter 112 of the inner needle tube 26 is noted. Similarly, the outer diameter 110 of the inner needle tube 26 is noted. According to the third column in the table 46 of FIG. 5, if the inner diameter 112 is 0.5 mm, the outer diameter 110 may be 0.8 mm, and if the inner diameter 112 is 0.4 mm, the outer diameter 110 may be 0.7 mm. Thus, the inner needle tube thickness 108 (FIG. 4) is 0.15 mm for these embodiments. Clearly, however, other diameter combinations are contemplated by the present invention. At the twelve o'clock position in FIG. 9 is the first side 84, which, as discussed above comprises the outer surface (i.e., the outer surface 134 of the outer needle tube 28 plus the outer surface 116 of the exposed portion 120 of the inner needle tube 26) of the conjoined inner and outer needle tubes 88 most closely adjacent to the puncture tip leading edge 90. As also discussed above, the second side 86 is offset from the first side 84 by 180°. Thus, the second side 86 is at the six o'clock position in FIG. 9.

FIG. 10 is a front view of the needle tip 96 depicted in FIGS. 4 and 7-9. This view clearly shows the needle longitudinal axis 48 and shows an inter-bevel angle 162 between the first tangential back bevel 152 and the second tangential back bevel 154. In this embodiment of the needle tip 96, the inter-bevel angle 162 is approximately 114°.

FIG. 11 is a side view of the needle tip 96. As shown in FIG. 11, the needle tip length 100, which is also depicted in FIG. 4, is the distance from the puncture tip leading edge 90 to the puncture tip trailing edge 98 measured in a direction parallel to the needle longitudinal axis 48. The needle tip 96 also includes a point length 163, which is the distance measured parallel to the needle longitudinal axis 48 between the puncture tip trailing edge 98 and a point 165 that is offset 180° from the puncture tip trailing edge 98 (similar to the puncture tip leading edge 90) and that also is on the projected outer surface 167 of the inner needle tube 26 where a projected wedge surface line 169 intersects the projected outer surface 167. When extended, the projected wedge surface line 169 passes through the puncture tip trailing edge 98, the needle longitudinal axis 48, the puncture tip leading edge 90, and the point 165.

In the needle tip 96 depicted in FIGS. 10-12, the point length 163 is approximately 0.67 mm (i.e., 0.026 inches). The first tangential back bevel 152 and the second tangential back bevel 154 each has a bevel length 164 as shown in FIG. 11. In this embodiment, the bevel length 164 is desirably 30-50% of the point length 163. For example, when the point length 163 is 0.67 mm, the bevel length 164 may be approximately 0.3 mm. FIG. 12 is a rear view of the needle tip 96 depicted in FIGS. 7-10 and clearly shows that with this tangential back beveled configuration, the first and second tangential back bevels (152, 154), although not visible in the front view (FIG. 10) of the needle tip 96, are clearly visible in the rear view.

Figures 13, 14:
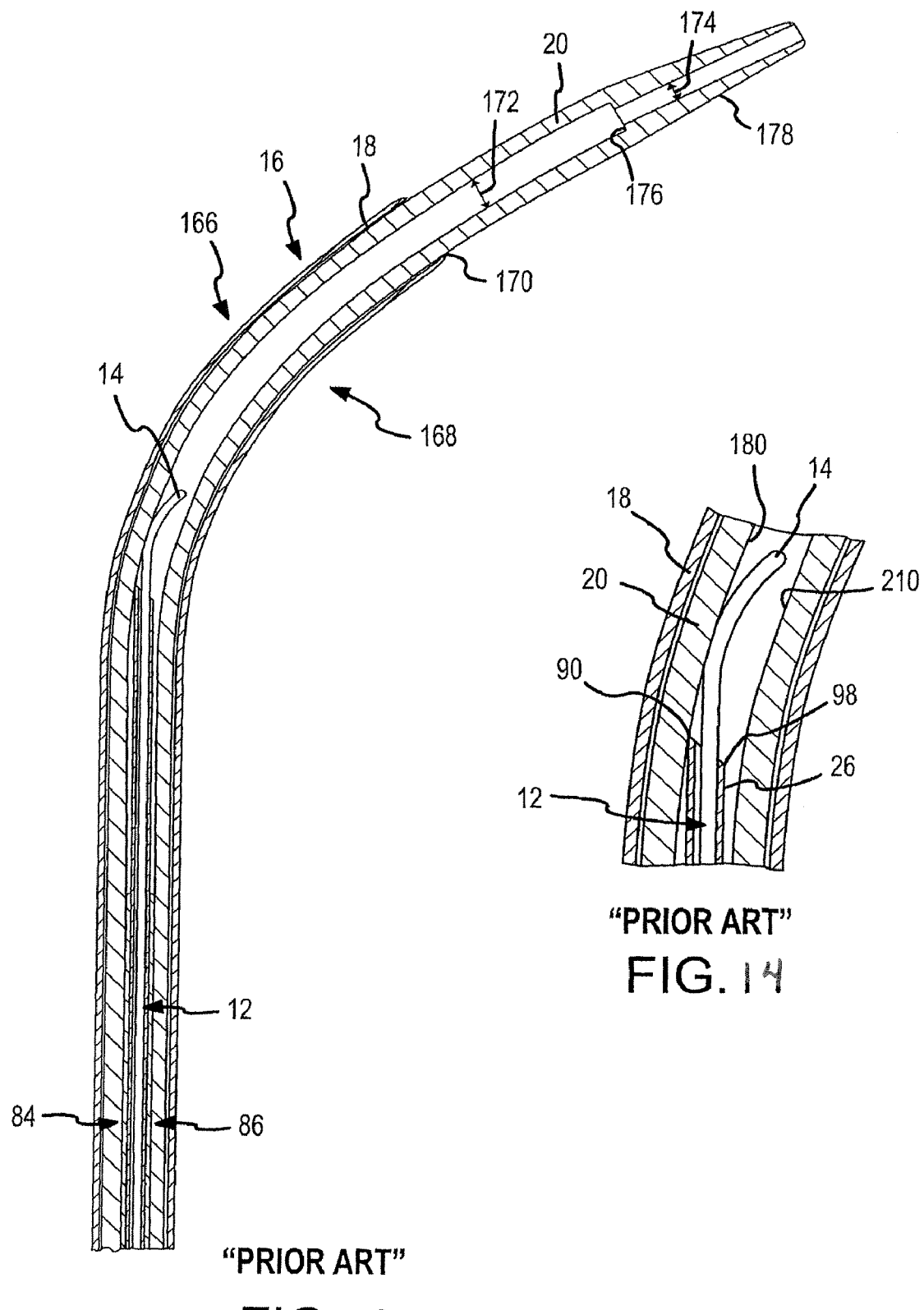
FIG. 13 is a fragmentary, cross sectional view of a curved transseptal puncture needle having the prior art tip configuration depicted in FIGS. 7-12 and a prior art axial orientation when partially inserted through a curved transseptal introducer.
FIG. 14 is an enlarged, fragmentary, cross sectional view of a portion of FIG. 13 to better show interaction between the puncture tip leading edge and the inner surface of the dilator.

FIG. 13 is a fragmentary, cross sectional view of a curved transseptal puncture needle 12 having the prior art tip configuration 96 depicted in FIGS. 7-12 and a prior art axial orientation relative to the curved transseptal introducer 16 through which it is being inserted. The curved transseptal introducer 16 has a convex side 166 and a concave side 168. The introducer 16 shown includes both a sheath 18 and a dilator 20, but the curved needles of the present invention may also be used with introducers that only have sheaths. As depicted in FIG. 13, the dilator 20 is extending from a distal end 170 of the sheath 18. The extended portion of the dilator necks down, from a first internal diameter 172 to a second internal diameter 174, creating an annular needle stop 176, as also mentioned below in connection with FIG. 15. The dilator 20 includes a frustal or tapered distal end 178. As shown in FIG. 13, in this prior art orientation of the curved transseptal puncture needle 12, the first side 84 of the needle 12 is on the convex curvature of the needle and its second side 86 is on the concave curvature of the needle. Thus, when the transseptal puncture needle 12 is forced through the introducer 16 as depicted in FIG. 13, the first side 84 of the needle 12 rides against the convex side 166 of the introducer 16, and the second side 86 of the needle 12 rides against the concave side 168 of the introducer 16.

As most clearly depicted in FIG. 14, since the first side 84 of the transseptal puncture needle 12 includes the puncture tip leading edge 90, when the needle 12 is forced through the introducer 16, the puncture tip leading edge 90 of the needle 12 scrapes along the inner surface 180 of the dilator 20 at the dilator's convex side 166 (the convex side 166 of the dilator 20 is, obviously, the same as the convex side 166 of the introducer 16). As a result, the transseptal puncture needle 12 is difficult to insert through the introducer 16 and is prone to remove dilator particulate as the needle 12 is advanced. This particulate material may undesirably end up in a patient's heart or blood stream.

Figure 15:
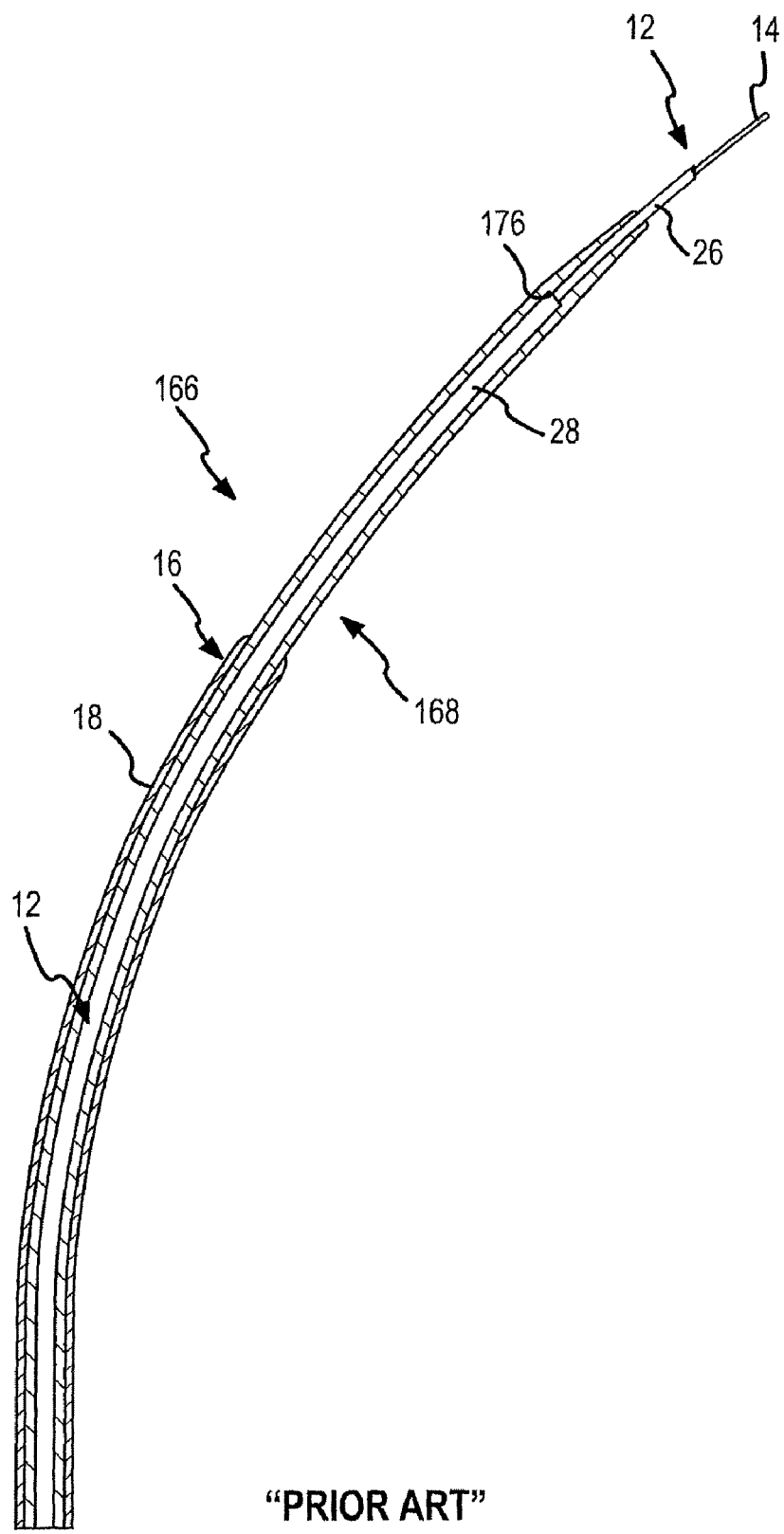
FIG. 15 is a fragmentary, cross sectional view similar to FIG. 13, but depicting the curved transseptal puncture needle fully inserted against the annular needle stop of the curved transseptal introducer with the stylet still in place.

FIG. 15 is similar to FIG. 13, but depicts the needle 12 after it has been fully inserted against the annular needle stop 176 of the curved transseptal introducer 16. The annular needle stop 176 helps prevent the physician from pushing the needle 12 too far through the introducer 16, which would otherwise cause an excessive portion of the transseptal puncture needle 12 to extend beyond the distal end of the dilator 20. From a comparison of FIG. 15 with FIG. 13, it is apparent that in some configurations, full insertion of the transseptal puncture needle 12 into the introducer 16 may cause the introducer 16 to straighten slightly. In other words, the introducer 16 is more sharply angled or curved in FIG. 13, where the transseptal puncture needle 12 is partially inserted in the introducer 16, than in FIG. 15, where the transseptal puncture needle 12 is fully inserted in the introducer 16. Thus, with the prior art needle tip configuration 96 and orientation depicted in FIGS. 13-15, the puncture tip leading edge 90 is closely adjacent to the outer surface 116 of the inner needle tube 26 and is oriented closely adjacent to the convex side 166 of the introducer 16. Thus, both the configuration and the axial orientation of the puncture tip 96 may contribute to possible removal of particulate material from the dilator 20 by the puncture tip leading edge 90.

FIGS. 16-19 depict one embodiment of a cannular or tubular needle tip 200 that may be utilized to good advantage in a transseptal needle 12 according to the present invention. One of ordinary skill in the art will appreciate that needle tip 200 may be provided proximate the distal end of an elongate needle body having a distal end and a proximal end, for example as shown in FIG. 1. Of course, a needle hub, such as shown at proximal end 22 in FIG. 1, may be coupled to the proximal end of the needle, and a stylet adapted for insertion through the needle body, such as stylet 14 shown in FIG. 1, may also be utilized.

Needle tip 200 generally includes a distal segment 202 and a proximal segment 204, as well as a longitudinal axis 206 (FIGS. 17-19) extending through at least a portion of distal segment 202 and proximal segment 204.

An inner surface 208 of needle tip 200 defines a passageway or lumen 210 that preferably spans at least a portion of needle tip 200. In some embodiments of the invention, passageway 210 may also extend through at least a portion of the elongate needle body (e.g., inner needle tube 26 as shown in FIG. 4). Between inner surface 208 and an outer surface 212, a wall 214 is defined.

One of ordinary skill in the art will recognize that needle tip 200 resembles, to a certain extent, a truncated cylinder that has been truncated in a way that results in a wedge surface 216 at distal segment 202. Wedge surface 216 forms a wedge angle 218 (FIG. 18) relative to longitudinal axis 206 of needle tip 200. Wedge angle 218 is preferably other than 90 degrees relative to longitudinal axis 206; in some embodiments of the invention, wedge angle 218 may be between about 20 degrees and about 50 degrees, and preferably is about 30 degrees. Of course, wedge angle 218 may be modified without departing from the scope of the invention.

Figure 18:
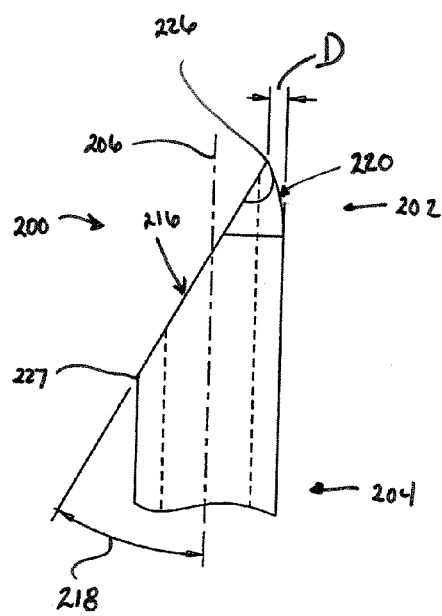
FIG. 18 is a side view of the transseptal puncture needle tip depicted in FIG. 17.
Figure 19:
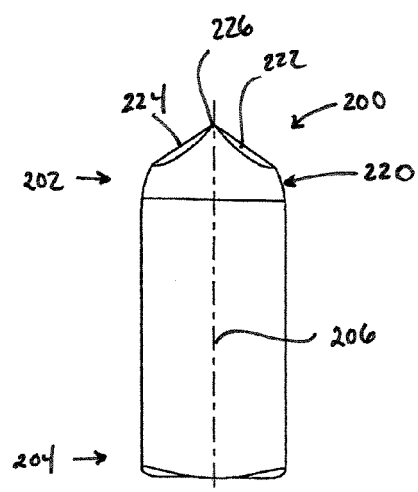
FIG. 19 is a rear view of the transseptal puncture needle tip depicted in FIG. 17.

As seen in FIGS. 18 and 19, the back side of distal segment 202 includes a dome-shaped region 220 that intersects with wedge surface 216. The term "dome-shaped region" is used herein to refer to a region where the generally cylindrical shape of needle tip 200 and/or needle tube/body 26 is altered to be curved. The term "dome-shaped region" is not limited to spherical or hemispherical domes, but is intended to broadly encompass all curvatures of outer surface 212 of needle tip 200 towards longitudinal axis 206 (thereby also reducing the thickness of wall 214 in dome-shaped region 220).

Dome-shaped region 220 has a depth D (FIG. 18), which is defined as the lateral distance between the "peak" of dome-shaped region 220 (e.g., where dome-shaped region 220 intersects wedge surface 216) and a vertical extension of the generally cylindrical shape of needle tip 200. Dome-shaped region 220 also has a radius of curvature. Preferably, the depth D of dome-shaped region 220 is between about 0.075 mm and about 0.125 mm, and more preferably the depth D is about 0.100 mm. Preferably, the radius of curvature of dome-shaped region 220 is between about 0.79 mm and about 0.99 mm, and more preferably the radius of curvature is about 0.89 mm. Of course, other dimensions are within the scope of the invention. One of ordinary skill in the art will appreciate that dome-shaped region 220 may have a single radius of curvature (e.g., is a spherical dome-shaped region) or multiple radii of curvature that may vary throughout dome-shaped region 220 (e.g., an elliptical dome-shaped region) without departing from the scope of the invention.

Within dome-shaped region 220 are first and second bevels 222, 224, respectively. First and second bevels 222, 224 may also be referred to as "tangential back bevels" or "reverse-angle bevels." First and second bevels 222, 224 intersect wedge surface 216; the intersection of first and second bevels 222, 224 with wedge surface 216 at least partially defines a puncture tip leading edge 226 to facilitate transseptal puncturing. Similarly, it should be understood that wedge surface 216 extends between puncture tip leading edge 226 and a puncture tip trailing edge 227.

Figure 16:
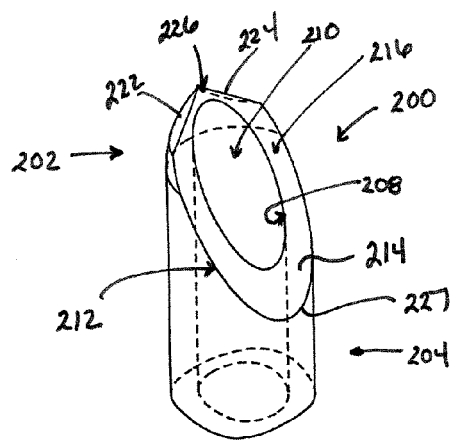
FIG. 16 is an enlarged, isometric view of a transseptal puncture needle tip according to one embodiment of the present invention.
Figure 17:
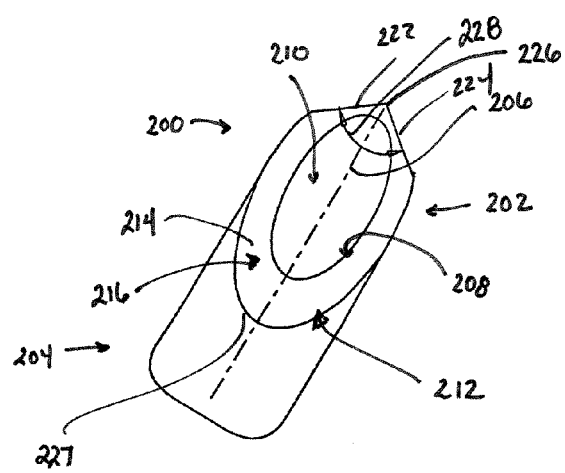
FIG. 17 is another view of the transseptal puncture needle tip depicted in FIG. 17.

As seen in FIGS. 16 and 17, bevels 222, 224 preferably are located to move puncture tip leading edge 226 towards inner surface 208 from outer surface 212, for example by positioning puncture tip leading edge 226 on an upper surface of wall 214. This advantageously diminishes the risk of skiving as the needle is advanced through the dilator or sheath.

As shown in FIGS. 16 and 17, first and second bevels 222, 224 typically intersect at one or more points within needle body 26, such as on needle tip 200. Preferably, first and second bevels 222, 224 intersect along a line (e.g., a line on needle tip 200), thereby forming an interbevel angle 228 (FIG. 17) therebetween. Preferably, interbevel angle 228 is between about 80 degrees and about 120 degrees, more preferably between about 100 degrees and about 110 degrees, and most preferably about 105 degrees. It is also desirable for the intersection between first and second bevels 222, 224 to be within wall 214, though it is within the scope of the invention for the intersection to be on inner surface 208 or outer surface 212 instead. The intersection of first and second bevels 222, 224 with each other, as well as with wedge surface 216, allows needle tip 200 to be sufficiently sharp and pointed so as to reduce the amount of insertion force required and reduce the likelihood of coring of tissue during transseptal puncture. Preferably, the needle tip 200 also provides sufficient feedback to the surgeon to let the surgeon know when the tissue has been punctured.

A transseptal needle according to some embodiments of the present invention may be manufactured as follows. First, a substantially tubular body, having a proximal end and a distal end, may be provided. Preferably, the distal end of the tubular body will include a dome-shaped region. The dome-shaped region may be created by bending the distal end of the substantially tubular body into a curve having the desired radius of curvature.

Next, the distal end of the substantially tubular body may be truncated at an angle to create a wedge surface. Preferably, the truncation, and therefore the wedge surface, intersects the dome-shaped region. Thus, the truncation may define the depth of the dome-shaped region.

Thereafter, at least one, and preferably at least two, reverse angle-bevels may be beveled into the dome-shaped region intersecting the wedge surface.

Figure 20:
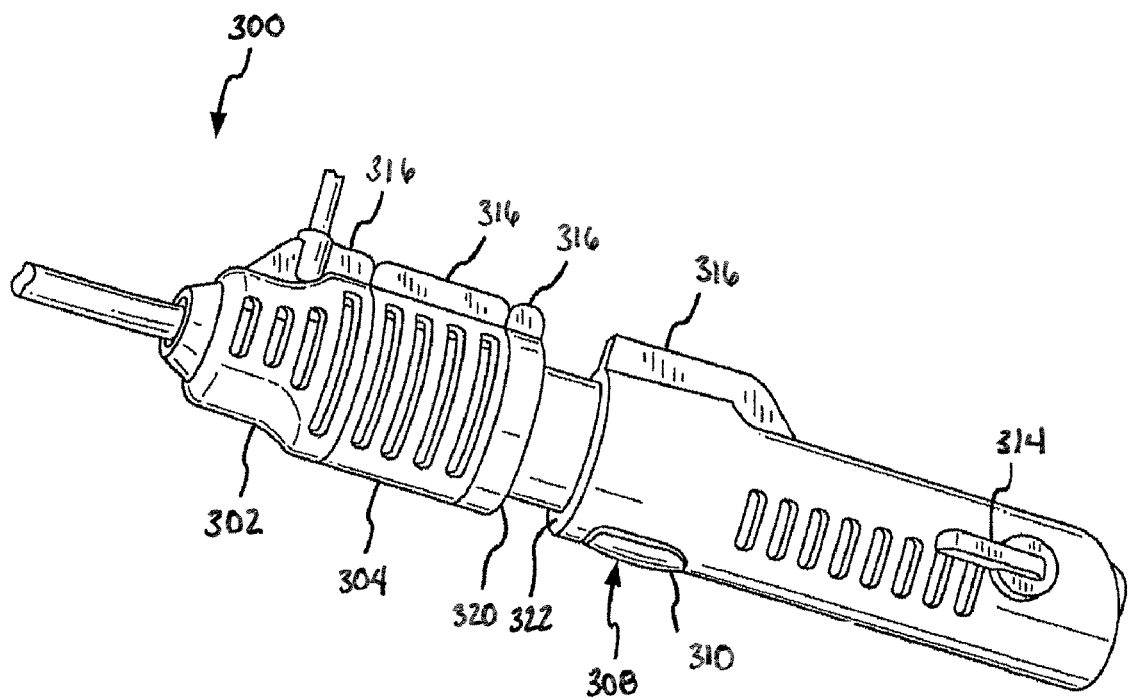
FIG. 20 is a perspective view of a handle assembly as may be used in accordance with some embodiments of the present invention.
Figure 21:
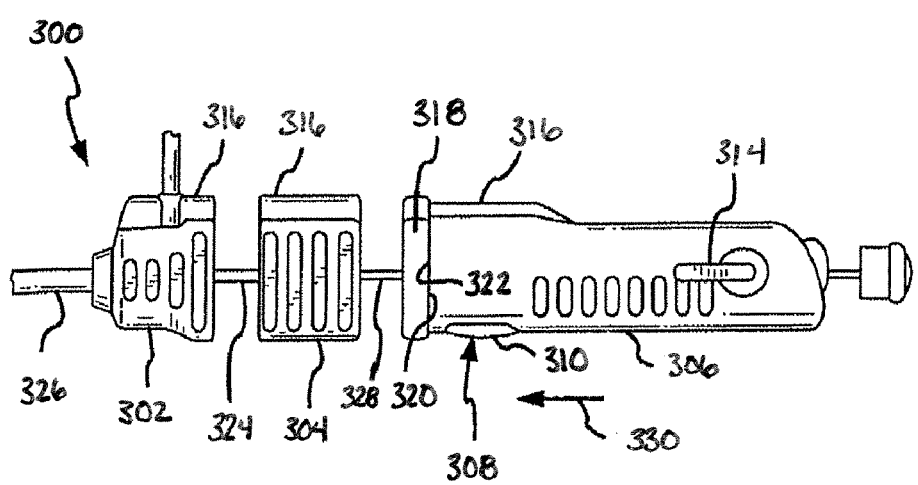
FIG. 21 is a side view of the handle assembly depicted in FIG. 20.

The present invention may also be practiced to good advantage in connection with a system for use in transseptal catheterization procedures including a handle assembly 300 such as illustrated in FIGS. 21 and 22. One of ordinary skill in the art will appreciate that such a system will generally include a needle (e.g., needle 328), a dilator (e.g., dilator 324), and a sheath (e.g., sheath 326), each having a corresponding hub assembly. Handle assembly 300 has cooperating hub assemblies for the sheath 302, dilator 304, and needle assemblies 306 typically used in transseptal procedures. The hub assemblies of each of these components are preferably preformed having corresponding removably attachable locking mechanisms (not shown). Suitable locking mechanisms include, for example, spring or lever biased latches for removable coupling. The assembly may also include a two-way adjustable valve 314 disposed within needle hub assembly 306. At least one of the hub assemblies may further include an orientation member, such as fin 316, that serves to visually identify the orientation of the particular assembly inside the body and to help maintain proper orientation of the members during a transseptal procedure. The configuration of the hub assemblies themselves may also be configured to allow for visual identification of the orientation of the assemblies within the body (e.g., in an elliptical cross-sectional shape as shown in FIG. 20).

Additionally, the embodiment of FIGS. 20 and 21 includes a needle stop mechanism 318 provided between the dilator hub 304 and the needle hub 306. The needle stop mechanism 318 is designed such that in the position shown in FIG. 20, the needle is contained at a predetermined position within the distal end of the dilator. In the default position, the needle stop mechanism 318 removably engages the dilator hub 304 and the needle hub 306 and maintains a predetermined distance between these hubs, corresponding to a desired distance between the distal end of the dilator and the distal end of the needle assembly. The needle stop mechanism 318 is removably coupled to needle hub 306 via a latch assembly 310 having a button 308 disposed on the outer surface of the needle hub 306. As shown in FIGS. 20 and 21, in order to advance the needle towards the distal end of the dilator, a physician (or any user) simply activates the needle advance mechanism 310 (e.g., presses button 308). Upon activation of button 308, the needle hub is released from the needle stop mechanism 318 and the dilator hub 304, thereby allowing for advancement of the needle assembly within the dilator a maximum distance corresponding to the distance between a needle stop interface 320 on the needle stop mechanism 318 and the distal end of the needle hub. This mechanism 318 provides for safe operation of the needle assembly by preventing movement of the needle assembly until desired activation by a user and further provides for accurate movement to a desired piercing position when the needle hub 306 is advanced to a point where the distal end 322 abuts the needle stop interface 320.

The sheath hub 302 and the dilator hub 304 may also have a corresponding snap lock feature that allows for temporary coupling of the two hub assemblies. FIG. 20 shows the dilator and sheath hubs in a locked position. After the puncture step is effected by the needle 328 (which may, of course, be as described above), as shown in FIG. 21 (or at any other desirable phase of the procedure), these assemblies may be separated from the needle stop assembly, and each other, to allow for insertion of either, or both, the dilator and the sheath across the punctured interatrial septum (see FIG. 4).

Although several embodiments of this invention have been described above with a certain degree of particularity, those skilled in the art could make numerous alterations to the disclosed embodiments without departing from the spirit or scope of this invention.

For example, though the invention has been described as having two bevels within the dome-shaped region, it is contemplated that additional bevels may be provided.

As another example, instead of using handle assembly 300 described herein, the present invention may be practiced with any of the handle assemblies disclosed in U.S. application Ser. No. 11/646,525. Further, needle tip 200 described herein may be employed with any of the transseptal needle embodiments disclosed in U.S. application Ser. No. 10/947,817. One of ordinary skill in the art will appreciate how to select a suitable handle assembly and/or needle assembly.

One of ordinary skill will also appreciate that suitable materials for needle assemblies according to the present invention include stainless steel, nickel titanium (e.g., Nitinol), and other biocompatible materials.

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A transseptal needle, comprising:
   an elongate needle body having a distal end and a proximal end;
   a cannular needle tip located proximate the distal end of the elongate needle body, the needle tip having a distal segment, a proximal segment, and a longitudinal axis extending through at least a portion of the distal segment and the proximal segment, the needle tip comprising:
   an inner surface defining a passageway spanning at least a portion of the needle tip;
   an outer surface,
   the inner surface and the outer surface defining therebetween a wall;
   a wedge surface at the distal segment of the needle tip, the wedge surface forming a wedge angle of other than 90 degrees relative to the longitudinal axis of the needle tip;
   a dome-shaped region at the distal segment of the needle tip;
   a first bevel in the dome-shaped region; and
   a second bevel in the dome-shaped region,
   wherein the first bevel and the second bevel intersect at one or more points on the needle tip, and
   wherein a puncture tip leading edge is at least partially defined by an intersection of the first bevel, the second bevel, and the wedge surface.

2. The transseptal needle according to claim 1, wherein the first bevel and the second bevel intersect along a line on the needle tip to form an interbevel angle.

3. The transseptal needle according to claim 2, wherein the interbevel angle is between about 80 degrees and about 120 degrees.

4. The transseptal needle according to claim 3, wherein the interbevel angle is between about 100 degrees and about 110 degrees.

5. The transseptal needle according to claim 4, wherein the interbevel angle is about 105 degrees.

6. The transseptal needle according to claim 1, wherein the first bevel and the second bevel intersect at one or more points within the wall.

7. The transseptal needle according to claim 1, wherein the first bevel and the second bevel intersect at one or more points on the inner surface.

8. The transseptal needle according to claim 1, wherein the dome-shaped region has a depth between about 0.075 mm and about 0.125 mm and a radius of curvature between about 0.79 mm and about 0.99 mm.

9. The transseptal needle according to claim 8, wherein the dome-shaped region has a depth of about 0.100 mm and a radius of curvature of about 0.89 mm.

10. The transseptal needle according to claim 1, wherein the wedge angle is between about 20 degrees and about 50 degrees relative to the longitudinal axis of the needle tip.

11. The transseptal needle according to claim 10, wherein the wedge angle is about 30 degrees relative to the longitudinal axis of the needle tip.

12. A transseptal needle assembly, comprising:
a tubular elongate needle body terminating in a needle tip, the needle tip comprising:
an inner surface defining a passageway extending through at least a portion of the needle body including the needle tip;
an outer surface;
a wedge surface;
a dome-shaped region intersecting the wedge surface; and
at least two reverse-angled bevels in the dome-shaped surface, each of the at least two reverse-angled bevels intersecting the wedge surface,
wherein the intersection of the at least two reverse-angled bevels and the wedge surface at least partially defines a puncture tip leading edge to facilitate transseptal puncturing.

13. The transseptal needle assembly according to claim 12, wherein the inner surface and the outer surface define therebetween a wall, and wherein the puncture tip leading edge is located on an upper surface of the wall.

14. The transseptal needle assembly according to claim 12, wherein the at least two reverse-angled bevels intersect at one or more points within the tubular elongate needle body.

15. The transseptal needle assembly according to claim 14, wherein the at least two reverse-angled bevels intersect along a line within the tubular elongate needle body.

16. The transseptal needle assembly according to claim 12, further comprising a needle hub coupled to the proximal end of the transseptal needle.

17. The transseptal needle assembly according to claim 12, further comprising a stylet adapted for insertion through the tubular elongate needle body.

18. A system for use in transseptal catheterization procedures, the system comprising:
a dilator;
a handle assembly including a sheath hub, a dilator hub removably connected to the sheath hub, and a needle hub removably connected to the dilator hub;
a needle assembly, the needle assembly including a transseptal needle having a needle tip, the needle tip comprising:
a wedge surface;
a dome-shaped region intersecting the wedge surface;
a first reverse-angle bevel in the dome-shaped surface intersecting the wedge surface; and
a second reverse-angle bevel in the dome-shaped surface intersecting the wedge surface and the first reverse-angle bevel; and
a needle advancement mechanism adapted to cooperate with the needle assembly, wherein the needle advancement mechanism allows for selective advancement of the needle assembly from a position within the dilator to a position external to the dilator.

19. An elongated, curved transseptal puncture needle, comprising:
a needle proximal end;
a needle distal end, wherein the needle distal end comprises a working portion including an inner needle tube and an outer needle tube, wherein the inner needle tube and the outer needle tube are conjoined, wherein the inner needle tube comprises a proximal end and a distal end, wherein the outer needle tube comprises a proximal end and a distal end, wherein the proximal end of the inner needle tube is inserted into the distal end of the outer needle tube, creating an embedded portion and an exposed portion of the inner needle tube, and creating a circumscribing portion and a nonoverlapping portion of the outer needle tube, and wherein the conjoined inner and outer needle tubes define a conjoined outer surface including an outer surface of the outer needle tube plus an outer surface of the exposed portion of the inner needle tube; and
a needle tip at the distal end of the inner needle tube, the needle tip comprising:
a puncture tip leading edge;
a puncture tip trailing edge;
a wedge surface extending between the puncture tip leading edge and the puncture tip trailing edge;
a dome-shaped region intersecting the wedge surface; and
a pair of intersecting reverse-angle bevels in the dome-shaped surface, each of the pair of intersecting reverse-angle bevels intersecting the wedge surface;
wherein the puncture tip leading edge is defined by an intersection of the pair of intersecting reverse-angle bevels and the wedge surface.

20. A method of manufacturing a transseptal needle, comprising the steps of:
providing a substantially tubular body having a proximal end and a distal end;
providing a dome-shaped region proximate the distal end;
truncating the substantially tubular body at a wedge angle to create a wedge surface, the wedge surface intersecting the dome-shaped region;
beveling a first reverse-angle bevel into the dome-shaped region intersecting the wedge surface; and
beveling a second reverse-angle bevel into the dome-shaped region intersecting the wedge surface,
thereby forming a puncturing tip leading edge.

21. The method according to claim 20, wherein the beveling step comprises:
wherein the first reverse-angle bevel and the second reverse-angle bevel intersect at an interbevel angle.

22. The method according to claim 20, wherein the at least one reverse-angle bevel intersects the wedge surface between an inner diameter of the substantially tubular body and an outer diameter of the substantially tubular body.

23. The method according to claim 20, wherein the step of providing a dome-shaped region proximate the distal end comprises bending the distal end of the substantially tubular body into a curved configuration prior to the truncating step.

* * * * *